(12) United States Patent
Schelper et al.

(10) Patent No.: US 8,563,781 B2
(45) Date of Patent: Oct. 22, 2013

(54) PROCESS FOR PREPARING KETONES, IN PARTICULAR MACROCYCLIC KETONES

(75) Inventors: Michael Schelper, Ludwigshafen (DE); Christoph Stock, Ellerstadt (DE); Klaus Ebel, Lampertheim (DE); Joaquim Henrique Teles, Waldsee (DE); Ralf Pelzer, Fürstenberg (DE)

(73) Assignee: BASF SE (DE)

( * ) Notice: Subject to any disclaimer, the term of this patent is extended or adjusted under 35 U.S.C. 154(b) by 196 days.

(21) Appl. No.: 13/269,016

(22) Filed: Oct. 7, 2011

(65) Prior Publication Data

US 2012/0088935 A1    Apr. 12, 2012

Related U.S. Application Data

(60) Provisional application No. 61/390,699, filed on Oct. 7, 2010.

(51) Int. Cl.
*C07C 45/27*   (2006.01)

(52) U.S. Cl.
USPC ........... 568/403; 568/363; 568/375; 568/379; 568/383

(58) Field of Classification Search
USPC .......................... 568/403, 363, 375, 379, 383
See application file for complete search history.

(56) References Cited

U.S. PATENT DOCUMENTS

| | | | |
|---|---|---|---|
| 3,778,483 A | 12/1973 | Becker et al. | |
| 4,967,033 A | 10/1990 | Mahaim | |
| 7,714,172 B2 | 5/2010 | Teles et al. | |
| 2011/0269996 A1 | 11/2011 | Teles et al. | |

FOREIGN PATENT DOCUMENTS

| | | |
|---|---|---|
| DE | 1668054 A1 | 2/1972 |
| DE | 2519817 A1 | 11/1976 |
| DE | 2916418 A1 | 11/1980 |
| EP | 0285420 A1 | 10/1988 |
| GB | 1551741 A | 8/1979 |
| WO | WO-2008/000756 A1 | 1/2008 |
| WO | WO-2010076182 | 7/2010 |

OTHER PUBLICATIONS

Bridson-Jones et al., "Oxidation of Organic Compounds by Nitrous Oxide", Journal of the Chemical Society, vol. 3009, (1951) p. 2.

Chapuis, et al., "Synthesis of Deuterium-Labeled Perfume Ingredients as Internal Standards for Their GC/MS Quantification", Helvetica Chimca Acta, vol. 92, No. 9, (2009), pp. 1782-1799 p. 1.
Fehr, et al., "A New α, β-Enone Alkynone Fragmentation. Syntheses of Exaltone® and (±) Muscone", Helvetica Chimca Acta, vol. 62, (1979), pp. 2655-2660.
Rautenstrauch, et al., "A Short Synthesis of (±)-Muscone", Helvetica Chimca Acta, vol. 73, (1990), p. 896, p. 9.
Starokon, et al., "A Liquid Phase Oxidation of Alkenes with Nitrous Oxide to Carbonyl Compounds", Adv. Synth. Catal., vol. 346, (2004), pp. 268-274, p. 1.

*Primary Examiner* — Elvis O Price
(74) *Attorney, Agent, or Firm* — Novak Druce Connolly Bove + Quigg LLP

(57) ABSTRACT

Ketones of the formula II

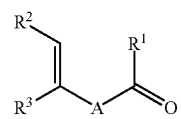

where A is optionally alkyl-substituted $C_2$-$C_{12}$-alkanediyl, $R^1$ and $R^2$ are each, independently of one another, $C_1$-$C_6$-alkyl, or $R^1$ and $R^2$ together form optionally alkyl-substituted $C_3$-$C_{10}$-alkanediyl, and $R^3$ is hydrogen or $C_1$-$C_6$-alkyl, are prepared by reacting a cyclic olefin of the formula I

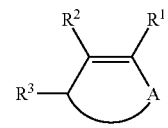

with dinitrogen monoxide to form the ketone of the formula II. The ketone of the formula II can be further hydrogenated to form the saturated ketone of the formula III.

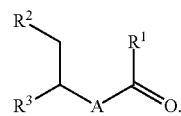

Macrocyclic ketones of the formula III, e.g. muscone, are sought after as fragrances.

15 Claims, No Drawings

PROCESS FOR PREPARING KETONES, IN PARTICULAR MACROCYCLIC KETONES

CROSS-REFERENCE TO RELATED APPLICATIONS

This application claims the benefit of U.S. Provisional Application 61/390,699, filed on Oct. 7, 2010, which is incorporated by reference.

BACKGROUND OF THE INVENTION

Saturated macrocyclic ketones having 14- to 18-membered rings, e.g. muscone (3-methylcyclopentadecanone), are sought-after fragrances or flavors. Since the compounds from natural sources are available only in small amounts, the synthesis of these has been the subject matter of comprehensive studies.

The preparation of muscone from 14-methylbicyclo[10.3.0]pentadecene[1(12)] has been known for a long time. Thus, CH-503 680 and U.S. Pat. No. 3,778,483 describe a process for preparing muscone, in which 14-methylbicyclo[10.3.0]pentadecene[1(12)] is oxidized by means of ozone to cleave the central double bond, a keto group of the resulting diketone is reduced to the alcohol and the unsaturated macrocyclic ketone obtained after elimination of water is hydrogenated to muscone.

V. Rautenstrauch et al., Helv. Chim. Acta Vol. 73, (1990), p. 896, describe a synthesis of muscone which starts out from 2-(2'-methylprop-2'-enyl)cyclododecan-1-one and proceeds via (3aRS,13aSR)-3a,4,5,6,7,8,9,10,11,12,13,13a-dodecahydro-2-methyl-1H-cyclopentacyclododecen-13a-ol. Further syntheses of muscone are described in DE 1 668 054 and Helv. Chim. Acta Vol. 62, (1979), p. 2657.

However, owing to the reagents used, their complexity and/or the yields achieved, the known processes are unsatisfactory. It is an object of the invention to provide a process by means of which particular saturated ketones, in particular saturated macrocyclic ketones such as muscone, can be obtained industrially in a simple way.

The oxidation of olefins by means of $N_2O$ to form an aldehyde or a ketone is a reaction which has been known for a long time and is described, for example, in GB 649,680. WO 2008/000756 describes a process for preparing a cyclic ketone having from 7 to 16 carbon atoms, in which a cyclic alkene having from 7 to 16 carbon atoms and at least one C=C double bond is oxidized by means of dinitrogen monoxide.

Cleavage of the C=C double bond usually does not occur or occurs to only a minor extent in this reaction. The exception is some strained rings systems such as bicycloheptene or indene; see E. V. Starokon, Adv. Synth. Catal. 2004, 346, 268-274.

The oxidation of tetrasubstituted olefins by means of $N_2O$ has hitherto been described only for the example of tetramethylethene. There, no cleavage of the C=C double bond was observed, see Bridson-Jones et al., JCS (1951), 3009.

BRIEF SUMMARY OF THE INVENTION

The invention provides a process for preparing ketones of the formula II,

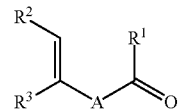

where
A is $C_2$-$C_{12}$-alkanediyl which is optionally substituted by from 1 to 5 $C_1$-$C_6$-alkyl groups,
$R^1$ and $R^2$ are each, independently of one another, $C_1$-$C_6$-alkyl or $R^1$ and $R^2$ together form $C_3$-$C_{10}$-alkanediyl which is optionally substituted by from 1 to 5 $C_1$-$C_6$-alkyl groups and
$R^3$ is hydrogen or $C_1$-$C_6$-alkyl;
wherein
(a) a cyclic olefin of the formula I

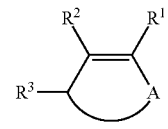

is reacted with dinitrogen monoxide ($N_2O$) to give the ketone of the formula II.

The invention further provides a process in which, in addition,
(b) the ketone of the formula II is hydrogenated to the saturated ketone of the formula III

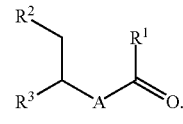

For the purposes of the present patent application, alkanediyl is preferably alkane-($\alpha,\omega$)-diyl.

DETAILED DESCRIPTION OF THE INVENTION

In the formulae I, II and III, A is $C_2$-$C_{12}$-alkanediyl, preferably $C_2$-$C_9$-alkanediyl such as ethane-1,2-diyl, propane-1,3-diyl, butane-1,4-diyl, pentane-1,5-diyl, hexane-1,6-diyl, heptane-1,7-diyl, octane-1,8-diylor nonane-1,9-diyl. A is preferably $C_3$-$C_9$-alkanediyl. The alkanediyl is optionally substituted by from 1 to 5 $C_1$-$C_6$-alkyl groups such as methyl, ethyl, propyl, isopropyl, butyl, sec-butyl, tert-butyl, pentyl or hexyl, in particular methyl.

$R^1$ and $R^2$ are each, independently of one another, $C_1$-$C_6$-alkyl such as methyl, ethyl, propyl, isopropyl, butyl, sec-butyl, tert-butyl, pentyl or hexyl.

As an alternative, $R^1$ and $R^2$ together form $C_3$-$C_{10}$-alkanediyl such as propane-1,3-diyl, butane-1,4-diyl, pentane-1,5-diyl, hexane-1,6-diyl, heptane-1,7-diyl, octane-1,8-diyl, nonane-1,9-diylor decane-1-10-diyl. $R^1$ and $R^2$ together preferably form $C_3$-alkanediyl or $C_4$-alkanediyl. If $R^1$ and $R^2$ together form alkanediyl, the cyclic olefin is a bicyclic compound in which the two rings have a common C=C double bond. The alkanediyl is optionally substituted by from 1 to 5 $C_1$-$C_6$-alkyl groups such as methyl, ethyl, propyl, isopropyl, butyl, sec-butyl, tert-butyl, pentyl or hexyl, in particular methyl.

$R^3$ is hydrogen or $C_1$-$C_6$-alkyl such as methyl, ethyl, propyl, isopropyl, butyl, sec-butyl, tert-butyl, pentyl or hexyl.

A preferred saturated ketone of the formula III which can be obtained by the process of the invention is (±)-3-methyl-cyclopentadecanone (muscone, racemic muscone or rac-muscone) of the formula IIIa

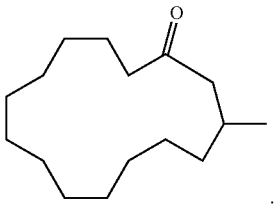
(IIIa)

For this purpose, 14-methylbicyclo[10.3.0]pentadecene[1 (12)] (2,3,4,5,6,7,8,9,10, 11,12,13-dodecahydro-2-methyl-1H-cyclopentacyclododecene) of the formula Ia is used as cyclic olefin of the formula I

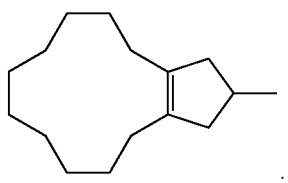
(Ia)

The compound Ia and its preparation are known. Ia can advantageously be obtained in the following way: cyclododecanone is reacted with a methallyl halide under the conditions of a phase-transfer reaction in the process as described in DE 29 16 418. The 2-(2'-methylene-1'-propyl)cyclododecanone obtained can be cyclized under acidic conditions in the gas phase as described in U.S. Pat. No. 4,967,033. This gives methylbicyclo[10.3.0]pentadecadiene in the form of various double bond isomers. This mixture is subsequently subjected to a palladium-catalyzed hydrogenation in which essentially only one double bond is hydrogenated and a double bond isomerization takes place at the same time, so that essentially Ia is obtained selectively, cf. Helvetica Chimica Acta 92 (9), 2009, 1782-1799, and DE 29 16 418 C2.

Other saturated ketones which can be prepared by the process of the invention are, for example, cyclopentadecanone(exaltone) and cyclohexadecanone.

In step (a) of the process of the invention, a cyclo addition of dinitrogen monoxide to form the adduct of the formula IV presumably takes place and this adduct is then rearranged with elimination of nitrogen to form the ketone of the formula II.

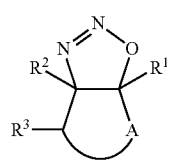
IV

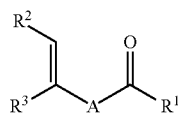
II

The ketone of the formula II has a double bond which can, in an undesirable secondary reaction, react again with dinitrogen monoxide to form a diketone. The conversion in step (a) is therefore preferably kept low, i.e. the reaction of the cyclic olefin of the formula I with dinitrogen monoxide is carried out only to a partial conversion. The partial conversion is preferably 20 mol % or less, in particular from 5 to 18 mol %, based on the initial amount of cyclic olefin of the formula I (in the case of a discontinuous process) or based on the cyclic olefin of the formula I in the feed (in the case of a continuous process). This gives a first mixture which comprises unreacted cyclic olefin of the formula I and ketone of the formula II. The first mixture can be worked up in various ways.

The first mixture can advantageously be subjected to a hydrogenation without prior separation.

A preferred embodiment therefore provides a process in which (i) the cyclic olefin of the formula I is reacted to a partial conversion with dinitrogen monoxide to give a first mixture which comprises unreacted cyclic olefin of the formula I and ketone of the formula II and (ii) the first mixture is hydrogenated under conditions under which the ketone of the formula II is hydrogenated to the saturated ketone of the formula III and the cyclic olefin of the formula I is essentially not hydrogenated, giving a second mixture which comprises unreacted cyclic olefin of the formula I and saturated ketone of the formula III.

The C=C double bond in the unsaturated ketone of the formula II is disubstituted (for $R^3$=H) or trisubstituted (for $R^{3'}C_1$-$C_6$-alkyl) and is therefore generally more reactive than the tetrasubstituted C=C double bond in the cyclic olefin of the formula I. The essentially selective-hydrogenation of the unsaturated ketone of the formula II therefore generally occurs without problems under suitable reaction conditions. For the purposes of the present process, it is generally sufficient for more than 90 mol % of the C=C double bond in the unsaturated ketone of the formula II and less than 10 mol % of the tetrasubstituted C=C double bond in the cyclic olefin of the formula I to be hydrogenated. The in principle undesirable hydrogenation of a small amount of the cyclic olefin of the formula I can be tolerated since the hydrogenation product of the cyclic olefin of the formula I is not reactive toward dinitrogen monoxide and can easily be separated from the desired reaction product by distillation.

Preference is given to recirculating at least part of the second mixture obtained in the hydrogenation to step (i) and subjecting it to renewed reaction with dinitrogen monoxide and again hydrogenating the resulting mixture. This procedure is repeated until a desired total conversion of the cyclic olefin of the formula I has been achieved or until the desired content of saturated ketone of the formula III in the product mixture has been reached. The product mixture is finally worked up.

As an alternative, the process of the invention can also be carried out continuously with part of the second mixture being admixed with fresh cyclic olefin of the formula I and recirculated to step (i) and part of the second mixture being taken off and saturated ketone of the formula III being isolated therefrom.

Another advantageous embodiment provides a process in which
(i) the cyclic olefin of the formula I is reacted to a partial conversion with dinitrogen monoxide to give a first mixture which comprises unreacted cyclic olefin of the formula I and ketone of the formula II and
(ii) unreacted cyclic olefin of the formula I is separated off from the first mixture to give a residue which comprises unsaturated ketone of the formula II and the residue is hydrogenated to give a hydrogenated residue which comprises saturated ketone of the formula III.

The unreacted cyclic olefin of the formula I is preferably separated off by distillation, with the residue comprising the unsaturated ketone of the formula II being obtained as bottom residue. The unreacted cyclic olefin which has been separated off is preferably at least partly recirculated to step (i), optionally together with fresh cyclic olefin of the formula I. The saturated ketone of the formula III can then be isolated from the hydrogenated residue.

In general, the addition of a solvent or diluent is not necessary in the reaction according to the invention with dinitrogen monoxide. Steps (a) and (b) are therefore advantageously carried out in the absence of an external solvent. External solvents are solvents which are not a starting material, product or by-product of the process of the invention.

The temperatures in the reaction of the cyclic olefin of the formula I with dinitrogen monoxide are generally in the range from 140 to 350° C., preferably in the range from 160 to 275° C. or in the range from 200 to 310° C. and particularly preferably in the range from 180 to 250° C. or from 250 to 300° C.

In the process of the invention, it is possible to carry out the reaction at two or more temperatures or in two or more temperature ranges which are in each case within the limits indicated above. Temperature changes in the course of the reaction can be carried out continuously or discontinuously.

The pressures in the reaction of the cyclic olefin of the formula I with dinitrogen monoxide are preferably higher than the autogenous pressure of the starting mixture or product mixture at the selected reaction temperature or the selected reaction temperatures. The reaction is preferably carried out under a pressure under which the dinitrogen monoxide is present in a condensed phase, i.e. liquid or supercritical phase. The pressures are preferably in the range from 1 to 1000 bar, more preferably in the range from 40 to 325 bar and particularly preferably in the range from 50 to 200 bar.

In the process of the invention, it is possible to carry out the reaction at two or more pressures or in two or more pressure ranges which are in each case within the limits indicated above. Pressure changes during the course of the reaction can be carried out continuously or discontinuously.

The reactors which can be used for the reaction are not subject to any particular restrictions. In particular, the reaction can be carried out batchwise or continuously. Accordingly, it is possible to use, for example, at least one CSTR (continuous stirred tank reactor) having at least one internal heat exchanger and/or at least one external heat exchanger, at least one tube reactor or at least one loop reactor as reactors. It is likewise possible to configure at least one of these reactors in such a way that it has at least two different zones. Such zones can, for example, differ in terms of reaction conditions, for example the temperature or the pressure, and/or in terms of the geometry of the zone, for example the volume or the cross section. If the reaction is carried out in two or more reactors, it is possible to use two or more of the same type of reactor or at least two different types of reactor.

The dinitrogen monoxide is advantageously introduced into the reactor as a liquid by means of a metering pump. However, it is also conceivable for gaseous dinitrogen monoxide to be dissolved beforehand in the cyclic olefin of the formula I or a feed mixture comprising the olefin under conditions under which no appreciable reaction occurs, in particular at a sufficiently low temperature, and this mixture then to be pumped into the reactor, e.g. by means of a metering pump.

In a preferred embodiment, the reaction with dinitrogen monoxide is carried out in a single reactor. In a further preferred embodiment, the reaction with dinitrogen monoxide is carried out in a single tube reactor.

The residence time of the reaction mixture in the at least one reactor is generally in the range up to 20 h, preferably in the range from 0.1 to 20 hours, more preferably in the range from 0.2 to 15 hours and particularly preferably in the range from 0.25 to 10 h.

The molar ratio of dinitrogen monoxide to the cyclic olefin of the formula I is generally in the range from 0.05 to 4, preferably in the range from 0.06 to 1, more preferably in the range from 0.07 to 0.5 and particularly preferably in the range from 0.1 to 0.4.

The hydrogenation of the ketone of the formula II can be carried out using any suitable catalysts. In particular, homogeneous and/or heterogeneous catalysts can be used. However, the hydrogenation is preferably carried out in the presence of a heterogeneous hydrogenation catalyst.

The catalysts which can be used preferably comprise at least one metal of transition group 7, 8, 9, 10 or 11 of the Periodic Table of the Elements. The catalysts which can be used more preferably comprise at least one element selected from the group consisting of Re, Fe, Ru, Co, Rh, Ir, Ni, Pd, Pt, Cu and Au.

In particular, the catalysts which can be used comprise at least one element selected from the group consisting of Fe, Ni, Pd, Pt and Cu. The catalysts used particularly preferably comprise Pd.

Homogeneous catalysts which are preferably used in the process of the invention comprise at least one element of transition group 8, 9 or 10. Greater preference is given to homogeneous catalysts which comprise Ru, Rh, Ir and/or Ni. Examples which may be mentioned here are $RhCl(TTP)_3$ ($TTP=Ph_2P(CH_2)_2PPh(CH_2)_2PPh_2$) or $Ru_4H_4(CO)_{12}$. Particular preference is given to homogeneous catalysts which comprise Ru. For example, use is made of homogeneous catalysts as are described in U.S. Pat. Nos. 5,180,870, 5,321, 176, 5,177,278, 3,804,914, 5,210,349 5,128,296, US B 316, 917 and in D. R. Fahey in J. Org. Chem. 38 (1973), pp. 80-87, which are fully incorporated by reference. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$ (TPP=triphenylphosphine).

In the process of the invention, particular preference is given to using at least one heterogeneous catalyst, with at least one of the abovementioned metals being able to be used as the metal itself, as Raney catalyst and/or applied to a customary support. Preferred support materials are, for instance, activated carbons or oxides such as aluminum oxides, silicon oxides, titanium oxides or zirconium oxides. Likewise, mention may be made of, inter alia, bentonites as support materials. If two or more metals are used, these can be present separately or as an alloy. It is here possible to use at least one metal as such and at least one other metal as Raney catalyst or at least one metal as such and at least one other metal applied to at least one support or at least one metal as Raney catalyst and at least one other metal applied to at least one support or at least one metal as such and at least one other metal as Raney catalyst and at least one other metal applied to at least one support.

The catalysts used in the process of the invention can, for example, also be precipitated catalysts. Such catalysts can be produced by precipitating their catalytically active components from their salt solutions, in particular from the solutions of their nitrates and/or acetates, for example by addition of solutions of alkali metal and/or alkaline earth metal hydroxide and/or carbonate, for example as sparingly soluble hydroxides, oxide hydrates, basic salts or carbonates, subsequently drying the precipitates obtained and then converting these by calcination at generally from 300 to 700° C., in particular from 400 to 600° C., into the corresponding oxides, mixed oxides and/or mixed-valence oxides which are reduced by treatment with hydrogen or with hydrogen-comprising gases at generally from 50 to 700° C., in particular from 100 to 400° C., to the corresponding metals and/or oxidic compounds of a lower oxidation state and converted into the actual catalytically active form. Here, the reduction is generally carried out until no more water is formed. In the production of precipitated catalysts which comprise a support material, the precipitation of the catalytically active components can be carried out in the presence of the support material concerned. The catalytically active components can advantageously be precipitated simultaneously with the support material from the appropriate salt solutions.

Preference is given to using hydrogenation catalysts which comprise the metals or metal compounds which catalyze the hydrogenation deposited on a support material in the process of the invention.

Apart from the abovementioned precipitated catalysts which further comprise a support material in addition to the catalytically active components, support materials in the case of which the catalytically hydrogenatively active component has, for example, been applied to a support material by impregnation are generally also suitable for the process of the invention.

The way in which the catalytically active metal is applied to the support is generally not critical and the application can be effected in various ways. The catalytically active metals can be applied to the support materials by, for example, impregnation with solutions or suspensions of the salts or oxides of the elements concerned, drying and subsequent reduction of the metal compounds to the respective metals or compounds in a lower oxidation state by means of a reducing agent, preferably by means of hydrogen or complex hydrides. Another possible way of applying the catalytically active metals to these supports is to impregnate the supports with solutions of readily thermally decomposable salts, for example nitrates or readily thermally decomposable complexes, for example carbonyl or hydrido complexes, of the catalytically active metals and heat the support which has been impregnated in this way to temperatures in the range from 300 to 600° C. to thermally decompose the adsorbed metal compounds. This thermal decomposition is preferably carried out under a protective gas atmosphere. Suitable protective gases are, for example, nitrogen, carbon dioxide, hydrogen or the noble gases. Furthermore, the catalytically active metals can be deposited on the catalyst support by vapor deposition or by flame spraying. The content of the catalytically active metals in these supported catalysts is in principle not critical for the success of the process of the invention. In general, higher contents of catalytically active metals in these supported catalysts lead to higher space-time yields than lower contents. In general, use is made of supported catalysts whose content of catalytically active metals is in the range from 0.1 to 90% by weight, preferably in the range from 0.5 to 40% by weight, based on the total weight of the catalyst. Since these indicated contents are based on the total catalyst including support material but the different support materials have very different densities and specific surface areas, it is also possible for the contents to be below or above these figures without this having an adverse effect on the result of the process of the invention. Of course, a plurality of the catalytically active metals can be applied to the respective support material. Furthermore, the catalytically active metals can be applied to the support by, for example, the method of DE-A 25 19 817 or EP 0 285 420 A1.

In the catalysts described in the abovementioned documents, the catalytically active metals are present as an alloy which is produced by thermal treatment and/or reduction of, for example, the support impregnated with a salt or complex of the abovementioned metals.

Both the activation of the precipitated catalysts and that of the supported catalysts can also occur in situ at the beginning of the reaction by means of the hydrogen present. These catalysts are preferably activated separately before use.

As support materials, it is generally possible to use the oxides of aluminum and titanium, zirconium dioxide, silicon dioxide, clay minerals such as montmorillonites, silicates such as magnesium or aluminum silicates, zeolites such as those of the structure types ZSM-5 or ZSM-10 or activated carbon. Preferred support materials are aluminum oxides, titanium dioxides, silicon dioxide, zirconium dioxide and activated carbon. Of course, mixtures of various support materials can also serve as support for catalysts which can be used in the process of the invention.

The at least one heterogeneous catalyst can, for example, be used as suspension catalyst and/or as fixed-bed catalyst.

If, for example, the hydrogenation in the process of the invention is carried out using at least one suspension catalyst, the hydrogenation is preferably carried out in at least one stirred reactor or in at least one bubble column or in at least one packed bubble column or in a combination of two or more identical or different reactors.

For the present purposes, the term "different reactors" refers both to different reactor types and to reactors of the same type which differ in terms of, for example, their geometry, for example their volume and/or cross section, and/or in terms of the hydrogenation conditions in the reactors.

If, for example, the hydrogenation in the process of the invention is carried out using at least one fixed-bed catalyst, preference is given to using at least one tube reactor, for example at least one shaft reactor, and/or at least one shell-and-tube reactor, with an individual reactor being able to be operated in the upflow mode or the downflow mode. When two or more reactors are used, at least one can be operated in the upflow mode and at least one can be operated in the downflow mode.

In a preferred embodiment of the process of the invention, the at least one catalyst used for the hydrogenation is separated off from the product mixture from the hydrogenation. This separation can, depending on the catalyst used, be carried out by any suitable method.

Since the presence of homogeneous hydrogenation catalysts does not adversely affect the reaction of the cyclic olefin of the formula I with dinitrogen monoxide, the removal of the catalyst from recycle streams can also be omitted.

If, for example, a heterogeneous catalyst is used in the hydrogenation as suspension catalyst, this is, for the purposes of the present invention, preferably separated off by means of at least one filtration step. The catalyst which has been separated off in this way can be recirculated to the hydrogenation or be fed to at least one other process. It is likewise possible to work up the catalyst, for example in order to recover the metal comprised in the catalyst.

If, for example, a homogeneous catalyst is used as catalyst in the hydrogenation, this is, for the purposes of the present invention, preferably separated off by means of at least one distillation step. One or two or more distillation columns can be used for this distillation. The catalyst which has been separated off in this way can be recirculated to the hydrogenation or fed to any other process. It is likewise possible to work up the catalyst, for example to recover the metal comprised in the catalyst.

Before use in any process, for example before recirculation to the process of the invention, both the at least one homogeneous catalyst and the at least one heterogeneous catalyst can, should it be necessary, be regenerated by means of at least one suitable process.

The removal of heat from the reactor used according to the invention can be effected internally, for example by means of cooling coils, and/or externally, for example by means of at least one heat exchanger. If, for example, at least one tube reactor is preferably used for the hydrogenation, the reaction is preferably carried out using an external circuit into which the heat removal is integrated.

If, in a preferred embodiment of the process of the invention, the hydrogenation is carried out continuously, further preference is given to using at least two reactors, more preferably at least two tube reactors, more preferably at least two tube reactors connected in series and particularly preferably two tube reactors connected in series. The hydrogenation conditions in the reactors used can in each case be identical or different and are in each case in the above-described ranges.

If the hydrogenation is carried out over at least one suspended catalyst, the residence time is generally in the range from 0.5 to 50 h, preferably in the range from 1 to 30 h and particularly preferably in the range from 1.5 to 25 h. Here, it is immaterial whether one reactor or at least two reactors connected in series are used for the purposes of the invention. In all these embodiments, the total residence time is in the abovementioned ranges.

If the hydrogenation in the process of the invention is carried out continuously over at least one fixed-bed catalyst, the residence time is generally in the range from 0.1 to 20 h, preferably in the range from 0.2 to 15 h and particularly preferably in the range from 0.3 to 10 h. It is immaterial whether one reactor or at least 2 reactors connected in series are used for the purposes of the invention. In all these embodiments, the total residence time is in the abovementioned ranges.

The hydrogen pressure in the hydrogenation is generally in the range from 1 to 325 bar, preferably in the range from 1.5 to 200 bar, more preferably in the range from 2 to 100 bar and particularly preferably in the range from 2.5 to 50 bar.

The hydrogenation temperature is generally in the range from 0 to 250° C., preferably in the range from 20 to 200° C., for example in the range from 30 to 180° C., more preferably in the range from 30 to 150° C., particularly preferably in the range from 40 to 170° C. and in particular in the range from 40 to 140° C.

The saturated ketone of the formula III is isolated from the product mixture obtained in the hydrogenation in a suitable way, for example by distillation. Here, the saturated ketone of the formula III is separated from high boilers, which consist essentially of diketone and decomposition products, and low boilers, which consist essentially of unreacted cyclic olefin of the formula I. The isolation and purification of the saturated ketone of the formula III can be carried out in one column or in two or three columns. It is also possible to use more columns, but this is generally not necessary.

The product mixture is preferably firstly introduced into the middle region of a (first) distillation column having internals. For this purpose, it is possible to use any distillation column. For the present purposes, the "middle region" of a distillation column is the region between top and bottom, i.e. the side inlet, of the distillation column.

As internals, it is possible to use any internals known to those skilled in the art. Preferred internals are selected from the group consisting of packing elements such as Pall rings and Raschig rings, structured packings made of metal sheet, e.g. Mellapak 250 from Sulzer Ltd. (Winterthur/Switzerland), Montz (Hilden/Germany) and Koch-Glitsch (Wichita, Kans./USA), and structured packings made of metal mesh, e.g. Sulzer BX (X3) from Sulzer Ltd. (Winterthur/Switzerland), Montz (Hilden/Germany) and Koch-Glitsch (Wichita, Kans./USA).

If the fractional distillation is carried out in only one column, preference is given to using a dividing wall column. Here, the low-boiling impurities are taken off at the top of the column and the high-boiling impurities are taken off at the bottom of the column. The stream taken off at the bottom of the column is firstly vaporized by means of a vaporizer. The vaporizable components are then recirculated to the column while the nonvolatile components, namely the low-boiling impurities, are discharged. The stream taken off at the top of the column is dealt with analogously. This stream is firstly condensed in a condenser and partly recirculated to the column for further fractionation. The desired product is taken off on the side of the dividing wall opposite the inlet in the upper region of the column, i.e. below the top of the column.

If two columns are connected to one another, the low-boiling impurities are separated off at the top of the first column and/or the second column and the high-boiling impurities are separated off at the bottom of the first column and/or the second column. It has been found to be advantageous to separate off the low-boiling impurities at the top of the first column.

The stream which has been freed of low-boiling impurities is discharged at the bottom of the first column. The stream discharged at the bottom of the column is then introduced into the middle region of the second column. The high-boiling impurities are taken off at the bottom of the column and discharged. The desired product is taken off at the top of the second column.

The low boilers, which consist essentially of unreacted cyclic olefin of the formula I, can advantageously be at least partly recirculated to step (a) of the process of the invention.

The invention is illustrated by the following examples.

EXAMPLE 1

Synthesis of 14-methylbicyclo[10.3.0]pentadecene[1(12)]

Step a): Alkylation of Cyclododecanone Using Methallyl Chloride 1458.4 g of cyclododecanone are dissolved in 1440 g of toluene and admixed with 30.4 g of tetrabutylammonium iodide. 1920 g of sodium hydroxide solution (50% strength) are added and the two-phase mixture is heated to 90° C. with vigorous stirring. 1087.2 g of methallyl chloride are then added dropwise over a period of 1 hour. After the addition is complete, the mixture is stirred at 90° C. for 5 h. It is allowed to cool to 60° C. and 1500 ml of water are added. The phases are separated and the organic phase is washed firstly with 2000 ml of water, then with 2000 ml of 10% strength $H_2SO_4$ and then with 2000 ml of 10% strength sodium hydroxide solution.

All low boilers are distilled off, and the product is subsequently purified by rectification. 2-(2-Methallyl)cyclododecanone goes over at 10 mbar, 164-165° C. A yield of 73% is obtained.

Step b): Gas-Phase Cyclization 70 ml (42.4 g) of aluminum oxide catalyst (1.5 mm extrudates, D10-10 from BASF SE, Germany, calcined at 500° C. under nitrogen for 5 h) are installed in a gas-phase apparatus which has a diameter of 1 cm and a length of 30 cm and is heated by means of an electric heating coil. At a reaction temperature of from 280° C. to 330° C., 10 g/h of 2-(2-methallyl)cyclododecanone (vaporization temperature: 290° C.) and 20 standard l/h of nitrogen as gas stream are introduced into the apparatus. Over a period of 190 h, 1905 g of starting material introduced gives 1755 g of cyclization product having a content of 72.3% of the main isomer (14-methylbicyclo[10.3.0]pentadeca-1,(12),13-diene) and 13.8% of secondary isomers. This material is used without further purification in the following step.

Step c): Diene Hydrogenation:

150 g of crude discharge from the gas-phase cyclization and 1.3 g of Pd/C catalyst (~5% of Pd, ~50% moisture (water)) are placed in a 300 ml autoclave provided with an inclined-blade stirrer. The autoclave is flushed with $H_2$ and the reaction mixture is subsequently heated to 100° C. When this temperature has been reached, the autoclave is pressurized with 5 bar of $H_2$ and the reaction is started. The $H_2$ pressure is kept constant at 5 bar during the course of the reaction. After the reaction is complete, the autoclave is cooled, depressurized and the catalyst is filtered off. The catalyst can be recirculated without a decrease in activity to a renewed hydrogenation. After a reaction time of 8 h, the diene conversion is 99.8% and the selectivity based on 14-methylbicyclo[10.3.0]pentadecene[1(12)] (Ia), the main isomer of the product, is 94.9%. The crude product obtained in this way, which has a content of 83.3% of main isomer and 7.8% of secondary components, is used without further purification in the following step.

EXAMPLE 2

Oxidation of (Ia) by Means of $N_2O$

The reaction was carried out in a tube reactor having a diameter of 1.7 mm and a total volume of 210 ml. The tube was provided with a double wall through which a heat transfer oil whose temperature was regulated by means of an external thermostat to 280° C. was circulated in order to thermostat the reactor. The reaction pressure was set to 270 bar by means of a pressure-regulating valve at the reactor output. The starting materials were metered continuously into the reactor by means of two metering pumps. Liquid $N_2O$ (Linde, 2.5, 25 g/h) was introduced by means of the first pump and the olefin (Ia) (150 g/h) was introduced by means of the second pump. The experiment ran for a total of 4 hours. The reactor discharge was, after depressurization, cooled, collected and analyzed by GC. The conversion of Ia was 10.3%. The selectivity to the desired product (3-methylcyclopentadec-5-enone and 3-methylcyclopentadec-4-enone, in each case as a mixture of the cis and trans isomers; this mixture is also referred to as muscenone) was 50.5%.

EXAMPLE 3

Hydrogenation of the Oxidation Discharge 1380 g of crude discharge from Example 2 (comprising 4.7% of muscenone, 74.2% of 14-methylbicyclo[10.3.0]pentadecene[1(12)], 4.3% of isomers of 14-methylbicyclo[10.3.0]pentadecene[1(12)] and 1.6% of diketones) and 11.0 g of Pd/C catalyst (~5% of Pd, ~50% of moisture (water) are placed in a 2.5l autoclave provided with a three-stage inclined-blade stirrer. The autoclave is flushed with $H_2$ and the reaction mixture is subsequently heated to 100° C. After this temperature has been reached, the autoclave is pressurized with 10 bar of $H_2$ and the reaction is started. The $H_2$ pressure is kept constant at 10 bar during the course of the reaction. After the reaction is complete, the autoclave is cooled, depressurized and the catalyst is filtered off. After a reaction time of 12 h, the muscenone conversion is 94.3% and the selectivity to muscone is 94.1%. The crude product obtained in this way is composed of 4.8% of muscone, 73.9% of 14-methylbicyclo[10.3.0]pentadecene[1(12)], 4.5% of isomers of 14-methylbicyclo[10.3.0]pentadecene[1(12)] and 1.6% of diketones and can either be separated by distillation or recirculated without further work-up to the oxidation.

The invention claimed is:

1. A process for preparing ketones of the formula II,

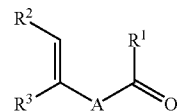

wherein
A is a $C_2$-$C_{12}$-alkanediyl which is optionally substituted by from 1 to 5 $C_1$-$C_6$-alkyl groups,
$R^1$ and $R^2$ are each, independently of one another, $C_1$-$C_6$-alkyl or $R^1$ and $R^2$ together form $C_3$-$C_{10}$-alkanediyl which is optionally substituted by from 1 to 5 $C_1$-$C_6$-alkyl groups, and
$R^3$ is hydrogen or a $C_1$-$C_6$-alkyl;
said process comprising:
(a) reacting a cyclic olefin of the formula I

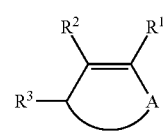

with dinitrogen monoxide to give the ketone of the formula II.

2. The process according to claim 1, further comprising
(b) hydrogenating the ketone of the formula II to the saturated ketone of the formula III

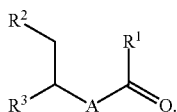

3. The process according to claim 2, wherein
(i) the cyclic olefin of the formula I is reacted to a partial conversion with dinitrogen monoxide to give a first mixture which comprises unreacted cyclic olefin of the formula I and ketone of the formula II and
(ii) the first mixture is hydrogenated under conditions such that the ketone of the formula II is hydrogenated to the saturated ketone of the formula III and the cyclic olefin of the formula I is essentially not hydrogenated, giving a second mixture which comprises unreacted cyclic olefin of the formula I and saturated ketone of the formula III.

4. The process according to claim 3, wherein at least part of the second mixture is recirculated to step (i).

5. The process according to claim 4, wherein steps (i) and (ii) are repeated until a desired total conversion of the cyclic olefin of the formula I has been achieved.

6. The process according to claim 4, wherein part of the second mixture is admixed with fresh cyclic olefin of the formula I and recirculated to step (i) and part of the second mixture is taken off and saturated ketone of the formula III is isolated therefrom.

7. The process according to claim 3, wherein the saturated ketone of the formula III is isolated from the second mixture by distillation.

8. The process according to claim 2, wherein
(i) the cyclic olefin of the formula I is reacted to a partial conversion with dinitrogen monoxide to give a first mixture which comprises unreacted cyclic olefin of the formula I and ketone of the formula II and
(ii) unreacted cyclic olefin of the formula I is separated off from the first mixture to give a residue which comprises unsaturated ketone of the formula II and the residue is hydrogenated to give a hydrogenated residue which comprises saturated ketone of the formula III.

9. The process according to claim 8, wherein the unreacted cyclic olefin of the formula I which has been separated off is at least partly recirculated to step (i).

10. The process according to claim 3, wherein the partial conversion is 20 mol % or less, based on the cyclic olefin of the formula I.

11. The process according to claim 1, wherein the reaction with dinitrogen monoxide is carried out in the absence of an external solvent.

12. The process according to claim 2, wherein the hydrogenation is carried out in the absence of an external solvent.

13. The process according to claim 1, wherein the reaction with dinitrogen monoxide is carried out under a pressure under which dinitrogen monoxide is present in a condensed phase.

14. The process according to claim 1, wherein the hydrogenation is carried out in the presence of a heterogeneous hydrogenation catalyst.

15. The process according to claim 2, wherein (±)-3-methylcyclopentadecanone of the formula IIIa is produced,

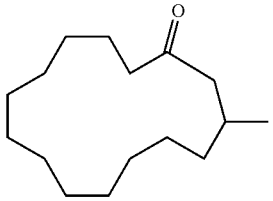

IIIa and wherein the cyclic olefin of the formula I is 14-methylbicyclo[10.3.0]pentadecene[1(12)] of the formula Ia

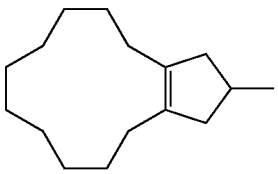

Ia

* * * * *